United States Patent [19]
Ognier et al.

[11] Patent Number: 5,178,606
[45] Date of Patent: Jan. 12, 1993

[54] IRRIGATION AND ASPIRATION APPARATUS FOR USE IN ENDOSCOPIC SURGERY

[75] Inventors: Jean-François Ognier, Saignes; Hubert Manhes, Vichy, both of France

[73] Assignee: Societe dite Sinergy S.A., a French Corp., Cusset, France

[21] Appl. No.: 582,980

[22] PCT Filed: Feb. 2, 1990

[86] PCT No.: PCT/FR90/00086
  § 371 Date: Oct. 1, 1990
  § 102(e) Date: Oct. 1, 1990

[87] PCT Pub. No.: WO90/08562
  PCT Pub. Date: Aug. 9, 1990

[30] Foreign Application Priority Data
  Feb. 2, 1989 [FR] France ............... 89 01648

[51] Int. Cl.$^5$ ............... A61M 1/00; A61M 31/00; A61F 7/12
[52] U.S. Cl. ............... 604/31; 604/67; 604/119; 604/114
[58] Field of Search ............... 128/DIG. 12; 604/27, 604/30, 31, 34, 43, 113, 114, 65–67, 118–121, 250

[56] References Cited

U.S. PATENT DOCUMENTS

| | | | |
|---|---|---|---|
| 986,618 | 3/1911 | Babler | 604/113 |
| 3,177,871 | 4/9165 | Meyers | 128/227 |
| 3,570,488 | 3/1971 | Diskin et al. | 604/31 |
| 3,900,022 | 8/1975 | Widran | 604/31 X |
| 3,943,065 | 1/1976 | Ginsberg et al. | 417/317 |
| 4,180,074 | 12/1979 | Murray et al. | 604/31 |
| 4,261,360 | 4/1981 | Perez | 604/31 |
| 4,486,389 | 12/1984 | Darnell et al. | 422/307 |
| 4,846,790 | 7/1989 | Hornlein et al. | 604/22 |
| 4,902,276 | 2/1990 | Zakko | 604/28 |
| 4,998,914 | 3/1991 | Wiest et al. | 604/67 |

FOREIGN PATENT DOCUMENTS

| | | | |
|---|---|---|---|
| 0403715 | 7/1934 | Belgium . | |
| 2378494 | 8/1978 | France . | |
| 1055521 | 4/1983 | U.S.S.R. | 604/113 |
| 1563795 | 4/1980 | United Kingdom | 604/113 |
| 2205244 | 12/1988 | United Kingdom . | |

Primary Examiner—C. Fred Rosenbaum
Assistant Examiner—Adam J. Cermak
Attorney, Agent, or Firm—Curtis, Morris & Safford

[57] ABSTRACT

The invention concerns a surgical apparatus for the irrigation and aspiration of the operative cavity during endoscopic surgery. The apparatus comprises a reservoir of liquid for irrigation of the cavity, a pump for circulating the liquid in the cavity, a pressure measuring and control means, such as a piezometric cell and valve for measuring and controlling pressure in the cavity and a flow control means for controlling the flow of the liquid. The apparatus also provides temperature control means by which the temperature of the liquid may be adjusted, which along with pressure control means and adjustment of pressure of the liquid in the cavity, provides a desired hemostatic effect during the surgical process.

10 Claims, 1 Drawing Sheet

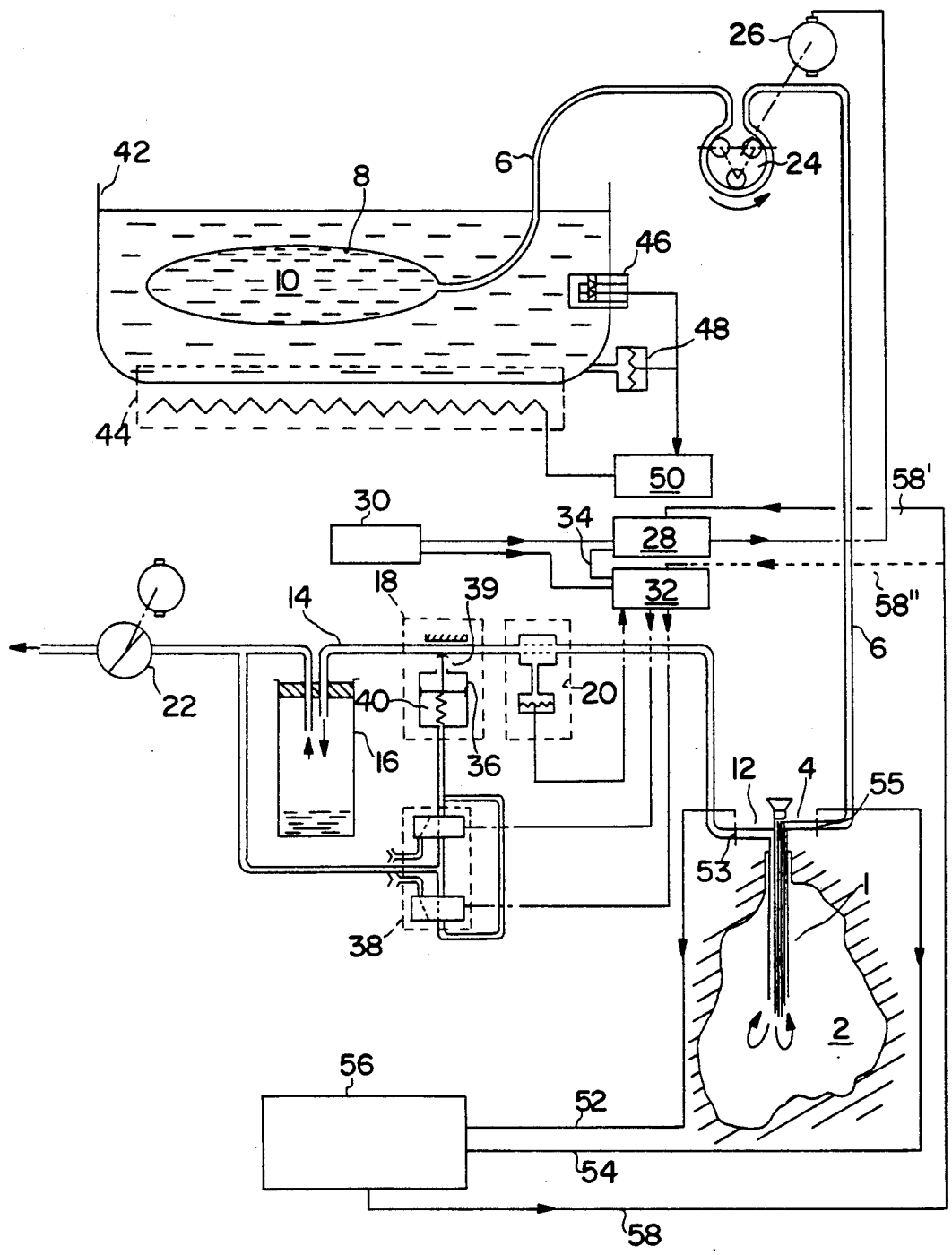

IRRIGATION AND ASPIRATION APPARATUS FOR USE IN ENDOSCOPIC SURGERY

BACKGROUND OF THE INVENTION

The present invention pertains to the field of surgical techniques and relates more particularly to an irrigation and aspiration apparatus which can be used in endoscopic surgery.

It will be recalled that endoscopic surgery and/or exploration generally makes use of irrigation means ensuring the cleaning of the operative site, aspiration means ensuring the removal of liquids and body tissues, and means for dilation or tensioning of the organs or of the cavity on which surgery is being carried out. The irrigation and dilation can be effected simultaneously by injection, under slight pressure, of an isotonic or very slightly hypotonic solution, such as advantageously glycine, on account of its dielectric properties. It will be remembered, as regards this surgical technique, that it is imperative to maintain the excess pressure between a minimum threshold (sufficient to dilate the cavity and to counterbalance the capillary pressure) and a maximum threshold (corresponding to the pressure of absorption of the irrigation liquid by the venous system). These thresholds, which vary between individuals, are approximately 15 and 45 mmHg respectively.

Irrigation techniques have been widely described, particularly in patent publications, and reference may advantageously be made to patents FR 2,244,440 (IGLESIAS), and FR 256,954, FR 2,569,555 (BURNER). The first of these patents describes simple means for supply of irrigation fluid consisting essentially of a gravity reservoir and of valves for controlling the flowrate. The BURNER patents describe more elaborate means, involving in particular the use of means for automatic regulation of the pressure using a pump placed under the control of a pressure regulator. The second of these latter patents describes more particularly an aspiration technique using means for regulating the pressure. However, it will be noted that even apparatuses with controlled pressure do not entirely rule out the risks of liquid passing into the blood system, on account of the significant variations in arterial pressure which can occur during surgery.

Publications WO 8700759 (MINNESOTA), FR 2,378,494 (WOLF) and U.S. Pat. No. 3,900,022 (WIDRAN) also disclose an irrigation device for injecting irrigation liquid into an operative cavity; however, these devices do not comprise means for heating the liquid or controlling its temperature. For related techniques, reference may also be made to the following publications: U.S. Pat. No. 4,486,384 (DARNELL), GB 2,205,244 (BLOGOVESCHENSKY), U.S. Pat. No. 3,177,871 (MYERS) and U.S. Pat. No. 4,702,733 (WRIGHT).

Finally, it is recalled that the haemostatic influence of temperature is well known, but that this influence is the result of two causes with different effects; on the one hand, a cause with a positive effect consisting in an increase in the rate of polymerization of the fibrinogens and the rate of formation of the "platelet clot"; on the other hand, a cause with a negative effect consisting in vasodilation.

As far as the Applicants are aware, no attempt has ever been made, in laparotomy surgery using an irrigation serum, to make use of the haemostatic influence of the temperature of the warm serum alone, because of the predominance of the negative effect; serum at 40°–45° C. has been used in particular, but after pinching or suturing the cut vessels. However, the Applicants considered that it might not be the same in endoscopic surgery on account of the positive effect of putting the operative cavity under excess pressure. Their work thus led them to note that a serum or other irrigation liquid injected at a temperature of between about 42° and 45° C. considerably slowed down the haemorrhagic flow; overall, the use of warm isotonic serum (42°–45° C.) instead of serum at ambient temperature, as in the prior art, has the following results: it accelerates the haemostasis of the vessels spread, permits a reduction in the irrigation flow necessary for cleaning the operative site and for maintaining perfect vision. There still remained the delicate problem of the risks of liquid being transferred into the blood system, with the peri- and postoperative risks which this involves, a problem for which the technique of the invention affords a solution. On the basis of these observations, the invention proposes means ensuring optimal irrigation of the operative site in endoscopic surgery, with a maximum limitation of the risk of the liquid passing into the blood system.

SUMMARY OF THE INVENTION

According to the present invention, an irrigation and aspiration apparatus for endoscopic surgery, of the apparatus type comprising a reservoir of irrigation liquid, a pump for circulating the liquid in the operative cavity, means for controlling the pressure in the said cavity and means for controlling the liquid flows, it being possible for the injection and removal of the liquid to be carried out with the aid of the operative or exploratory instrument used, is principally characterized in that it additionally comprises means for heating and/or maintaining the temperature of the irrigation liquid, in a temperature control range of between 40° and 50° C., and means for maintaining the excess pressure of the said liquid in the said cavity, the excess pressure being adjustable in a range from 40 to 80 mm/Hg. According to the invention, these means co-operate, on the one hand, to oppose the blood flow through connections in the damaged vessels and, on the other hand, when the blood flow has been stopped, to coagulate the blood there by means of the haemostatic effect of the temperature.

In a second arrangement, the device according to the invention also comprises means for differential measurement between the injected volumes and the recovered volumes; means can advantageously be provided for processing these measurements and supplying an instantaneous differential measurement, cumulative measurements, or even for acting on the means for generating the excess pressure in the cavity. Thus, the serum passes successively from the reservoir into a peristaltic pump, then into the cavity by way of the instrument, then into a piezometric cell measuring the excess pressure in the cavity, then into a valve for controlling the pressure inside the cavity, and is finally received in a chamber under low pressure.

The peristaltic pump is advantageously driven under the control of both manual means for regulating the flowrate and automatic stop means in the case of excess pressure in the cavity, while the valve for controlling the pressure inside the cavity is placed under the control of piezometric means for measuring the excess pressure in the cavity; the pump and/or the valve may, if appropriate, as indicated above, also be placed under the control of means for measuring or calculating the liquid flowrates.

According to a particular embodiment, the regulating valve is of the type involving squeezing of a pipe by a spring-finger, the said spring-finger being moved by a pneumatic jack acted upon in the open position by the low pressure prevailing in the said chamber, and in the closed position by a spring acting counter to the low pressure.

According to another particular embodiment, the means for heating and/or maintaining the temperature consist of a waterbath in which at least one bag containing the irrigation liquid floats freely; however, the waterbath is advantageously made sufficiently large so as to be able to contain several bags, for example two bags of so-called "physiological" liquid and two bags of Ringer's solution.

According to another particular embodiment, a means for heating the said waterbath consists of an electrical resistor placed under the control of a regulating thermostat with a top temperature threshold and bottom temperature threshold approximately 2° C. apart, these thresholds being adjustable. By way of example, a bottom trigger threshold of 42° C. and a top stoppage threshold of 44° C. can be chosen. A safety thermostat with a top stoppage threshold of 50° C. may also be provided.

Finally, and advantageously, a continuous flexible tube connects the said bag floating in the waterbath to an inlet nozzle on the said instrument, the said continuous flexible tube constituting the pipe of the peristaltic pump; the reservoir is advantageously a flexible bag.

According to an advantageous arrangement, the flexible tube intended to connect the bag to the instrument constitutes, together with the bag, a sterile packing of the irrigation liquid, and the flexible tube connecting the receiving chamber to the said control valve, on the one hand, and to a vacuum pump, on the other hand, constitutes, together with the chamber, a sterile packing of the recovered irrigation liquid.

The present invention will be better understood and details pertaining to it will emerge from the following description of a particular and preferred embodiment of the invention, with reference to the FIGURE on the single plate attached, which is a diagrammatic representation of the apparatus according to the invention.

BRIEF DESCRIPTION OF THE DRAWING

In the FIGURE, an instrument for endoscopic surgery 1, for example an instrument of the type described in a patent application FR 88/00,170, is introduced into a body cavity 2; a first nozzle 4 on the instrument is connected via a first continuous flexible tube 6 to a flexible bag 8, constituting the reservoir mentioned above, and containing an irrigation liquid 10, while a second outlet nozzle 12 is connected via a second flexible tube 14 to a receiving chamber 16 under low pressure; a pipe-squeezing valve 18 is inserted on the second flexible tube between the outlet 12 from the instrument and the chamber 16, while a piezometric cell 20 is passed through by the liquid downstream of the instrument and upstream of the valve. A vacuum pump 22 establishes a greatly reduced pressure in the chamber 16.

A peristaltic pump 24 driven by a motor 26 acts on the flexible tube so as to transfer the liquid 10 from the bag 8 towards the cavity 2; the motor 26 for driving the pump is controlled in terms of its rotation by means 28 which are manually adjustable from a keyboard 30; the pump flowrate 26 is adjustable from 0 to 700 ml/min.

The keyboard 30 also permits adjustment, via the control means 32, of the excess pressure in the cavity 2, the control means 32 being in communication with the piezometric cell 20; it will also be noted that the control means 32 also have a connection 34 to the means 28 for controlling the rotational speed of the pump, in order to stop the latter in the event of an excess pressure threshold (about 50 mm/Hg) being exceeded in the cavity 2.

The valve 18 consists of the flexible wall of the tube 14 and of a finger 39 mounted at the end of the rod of a jack 36; this arrangement provides for suitable sterility conditions downstream of the cavity; an electromagnetically controlled valve gear 38 brings the jack into communication either with the atmosphere or with the inlet of the vacuum pump 22; a spring 40 stresses the finger in the closure position. It should be understood that any other mechanism effecting the manoeuvre of the spring-finger, for example electromagnetic, mechanical, numerical or analog control, could replace the pneumatic mechanism mentioned above.

The bag 8 floats freely in the waterbath 42; the latter is heated by an electrical resistor 44 under the control of temperature-regulating means 50 comprising a couple 46 of thermistors (or another heat-measuring device with two thresholds); means 48, for example piezometric, can prevent heating if there is insufficient water in the waterbath.

According to an advantageous alternative arrangement, the bag 8 and the flexible tube 6 constitute a sterile packing of the liquid which they contain when put at the disposal of the practitioner, who is responsible for connecting it in a sterile manner to the instrument and for inserting the middle part of the tube in the pump 24.

Lines 52 and 54 show the transmission lines of signals coming from flowrate sensors 53 and 55 arranged at the inlet and outlet of the instrument 1 near the nozzles 4 and 12, and in the direction of a control assembly 56. These flowrate sensors will preferably have no contact with the passing fluid, such as, for example, electromagnetic or ultrasound sensors; the assembly 56 provides the reading of the instantaneous flowrates, integrates their difference and accumulates these measurements and their difference, so as to provide a possibility of controlling a possible passage, instantaneous or accumulated, of liquid into the blood system. By way of a line 58(58',58") the assembly 56 can act, as a function of the volumetric measurements, on the means 28 for controlling the pump 24 and/or on the means 32 for controlling the valve 18; the control assembly 56 can incorporate sensitive signalling means, for example sound means, for indicating instantly to the practitioner the exceeding of certain flowrate thresholds.

Another simple way of measuring a possible passage of irrigation liquid into the blood system consists, again according to the invention, in the precise and permanent weighing, for example by strain gauges, of the whole apparatus and liquid, upstream and downstream of the instrument: in the absence of any passage of liquid towards the blood system, the weight of the assembly must be constant; signalling means similar to those used in the volumetric method described above can be used in this gravimetric method.

Although a particular embodiment of the irrigation apparatus according to the invention has been described and illustrated, it should be understood that the scope of the latter is not limited to this embodiment, but instead extends to any irrigation apparatus comprising, separately or in combination, the general characteristics set out above.

We claim:

1. A surgical apparatus for the irrigation and aspiration of the operative cavity during endoscopic surgery, which apparatus provides a hemostatic effect during the surgical process, said apparatus comprising:
   a reservoir of liquid for irrigating the cavity;
   a pump for circulating the liquid in the cavity;
   a means for controlling liquid pressure and flow in the cavity which means permits the introduction and removal of liquid from the cavity; wherein the apparatus further comprises:
   a temperature control means by which the temperature of the irrigation liquid can be maintained between 40° to 50° C.; and
   a pressure control means by which pressure of the liquid in the cavity can be adjusted to the range of from 40 to 50 mm/Hg.

2. The apparatus as in claim 1, further comprising a volume measuring means for measuring the difference between the volume of liquid introduced and volume of liquid removed from the cavity; and
   a pressure measuring means for measuring excess liquid pressure in the operative cavity.

3. The apparatus as in claim 1, wherein the pump is a peristaltic pump which is in line with the reservoir, and which pump passes the liquid into the operative cavity, and which apparatus further comprises
   a piezometric cell which cell measures the excess liquid pressure in the cavity,
   a valve which valve controls the liquid pressure inside the cavity and
   a receiving chamber into which the liquid is received.

4. The apparatus as in claim 3, wherein the peristaltic pump further comprises a manual means and an automatic flow rate regulating means which means control the pump, which automatic means comprises a valve, which valve is controlled by the piezometric cell which cell measures the excess pressure in the cavity.

5. The apparatus as in claim 1, further comprising an operative instrument and a continuous flexible tube, which tube connects the reservoir to the operative instrument, said operative instrument having an inlet nozzle to which the flexible tube is connected, said flexible tube being continuous and constituting a portion of the peristaltic pump.

6. The apparatus as in claim 5, wherein said reservoir is a flexible bag.

7. The apparatus as in claim 6, wherein the flexible tube which connects the bag and the instrument comprises, with the bag, a sterile container for the irrigation liquid, further characterized in that the flexible tube at one end connects the receiving chamber to the control valve and at the other end to a vacuum pump, which apparatus further comprises, with the chamber, a sterile container for recovered irrigation liquid.

8. The apparatus as in claim 1, wherein the temperature control means comprises a waterbath wherein the reservoir containing the irrigation liquid floats.

9. The apparatus as in claim 8, further comprising a means for controlling the temperature of said waterbath, which means comprises an electrical resistor controlled by a regulating thermostat which has a bottom trigger threshold and a top stoppage threshold, which thresholds are approximately 2° C. apart in temperature.

10. A surgical apparatus for the irrigation and aspiration of the operative cavity during endoscopic surgery, which apparatus provides a hemostatic effect during the surgical process, said apparatus comprising:
    a reservoir of liquid for irrigating the cavity;
    a peristaltic pump in line with the reservoir and which pump passes the liquid into the operative cavity;
    a piezometric cell which cell measures the excess liquid pressure in the cavity;
    a valve, which valve controls the liquid pressure inside the cavity and which valve comprises a pipe, a springfinger and a pneumatic jack, which jack may move from an open to a closed position wherein the pipe may be squeezed by the springfinger, and wherein the springfinger moves by means of the pneumatic jack which jack is acted upon in the open position by low pressure, which low pressure prevails in the chamber, and in the closed position by a spring, which acts counter to the low pressure;
    a temperature control means by which the temperature of the irrigation liquid can be maintained between 40° to 50° C.; and
    a pressure control means by which pressure of the liquid in the cavity can be adjusted to the range of from 40 to 50 mm/Hg, and
    a receiving chamber into which the liquid is received.

* * * * *